US011364239B2

(12) United States Patent
Singh

(10) Patent No.: US 11,364,239 B2
(45) Date of Patent: Jun. 21, 2022

(54) COMPOSITIONS AND METHODS FOR MITIGATING AFLATOXIN B1-INDUCED LIVER INJURY

(71) Applicant: CFD Research Corporation, Huntsville, AL (US)

(72) Inventor: Narender Singh, Madison, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 0 days.

(21) Appl. No.: 16/862,500

(22) Filed: Apr. 29, 2020

(65) Prior Publication Data

US 2021/0338664 A1 Nov. 4, 2021

(51) Int. Cl.
*A61K 31/34* (2006.01)
*A61K 31/665* (2006.01)
(Continued)

(52) U.S. Cl.
CPC .......... *A61K 31/497* (2013.01); *A61K 31/341* (2013.01); *A61K 31/661* (2013.01); *A61P 1/16* (2018.01)

(58) Field of Classification Search
CPC ........... A61K 31/341; A61P 39/02; A61P 1/16
(Continued)

(56) References Cited

U.S. PATENT DOCUMENTS

2003/0191137 A1   10/2003  Kim et al.
2009/0149551 A1    6/2009  Zhou et al.

FOREIGN PATENT DOCUMENTS

CN          104083386 A      10/2014

OTHER PUBLICATIONS

Wire et al. "Fosamprenavir Clinical pharmacokinetics and Drug interactions of the amprenavir prodrug," Clin. Pharmacokinet. 2006, vol. 45, No. 2, pp. 137-168 (Year: 2006).*

(Continued)

*Primary Examiner* — Shengjun Wang
(74) *Attorney, Agent, or Firm* — Maschoff Brennan; Jonathan M. Benns

(57) ABSTRACT

A method for providing a therapy to a subject that has been exposed to an Aflatoxin B1 can include administering a compound having a structure of Formula 1 to the subject after exposure to the Aflatoxin B1:

Figure 1:
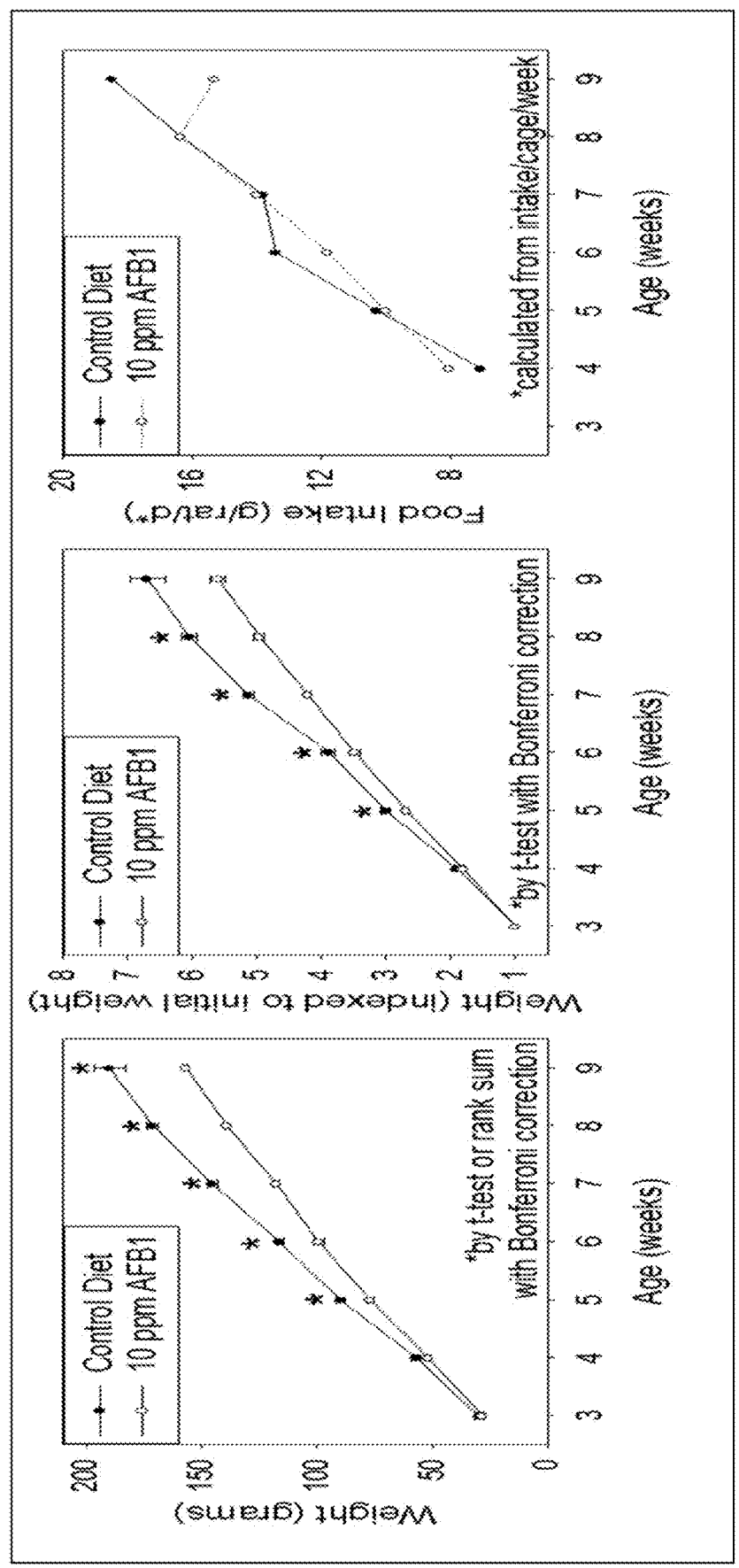

Formula 1 wherein: $R^1$, $R^2$, $R^3$, $R^4$, $R^5$ and/or $R^6$ are each individually a chemical moiety and n is 1, 2, 3, 4, or 5. The compound can be Amprenavir or a derivative thereof, prodrug thereof, salt thereof, or stereoisomer thereof, or having any chirality at any chiral center, or tautomer, (Continued)

polymorph, solvate, or combination thereof. The prodrug can be Amprenavir phosphate.

19 Claims, 9 Drawing Sheets

(51) Int. Cl.
*A61K 31/497* (2006.01)
*A61P 1/16* (2006.01)
*A61K 31/341* (2006.01)
*A61K 31/661* (2006.01)

(58) Field of Classification Search
USPC .......................................................... 514/471
See application file for complete search history.

(56) References Cited

OTHER PUBLICATIONS

Kamdem et al. "Dominant contribution of P450 3A4 to the hepatic Carcinogenic Activation of Aflatoxin B1," Chem. Res. Toxicol. 2006, vol. 19, pp. 577-586 (Year: 2006).*

* cited by examiner

*Calculated from concentration in food, food intake, and body weight
Target dosing: low - 20 mg/kg/d; medium - 100 mg/kg/d; high - 400 mg/kg/d

COMPOSITIONS AND METHODS FOR MITIGATING AFLATOXIN B1-INDUCED LIVER INJURY

STATEMENT OF GOVERNMENT SUPPORT

This invention was made with government support under W911QY-17-C-0008 awarded by U.S. Department of Defense—Chemical Biological Defense. The government has certain rights in the invention.

BACKGROUND

Field

The present disclosure relates to compounds and/or materials for use in mitigating toxicity of an aflatoxin. More particularly, the compounds and/or materials can be used for mitigating toxicity of the Aflatoxin B1 in order to mitigate liver injury caused by the aflatoxin.

Description of Related Art

Previously, it has been known that aflatoxins are poisonous carcinogens and mutagens that are generated by some molds that are commonly found in decaying vegetation or soil. The aflatoxins are often found to be contaminants in various staple commodities, which results in exposure to animals, such as humans and agricultural animals. Unfortunately, animals that consume the aflatoxin can pass it to the human in eggs, milk products, or meat products. As a result, humans, especially children, can suffer the adverse effects of aflatoxin exposure.

Some aflatoxins are mycotoxins, which are secondary metabolites of several fungi produced in particular conditions of humidity, temperature and pH. Among mycotoxins, Aflatoxin B1, produced by *Aspergillus* species are of special concern. These fungi infect food crops, such as maize and tree nuts, leading to a global exposure of about 4.5 billion people a year to Aflatoxin B1 through diet. The International Agency for Research on Cancer (IARC) has classified "naturally occurring mixture of Aflatoxin B1" as a Group 1 human carcinogen, and in this group Aflatoxin B1 is the most toxic agent. Aflatoxin B1 exposures leads to acute effects, including rapid death, and chronic outcomes such as hepatocarcinoma and stunned growth in children. It has also been demonstrated that even low toxin levels in the diet can cause to multiplicatively increase the risk of liver cancer in people chronically infected with hepatitis B virus along with effecting immune, reproductive, and digestive systems.

Overall the putative mechanism of action of Aflatoxin B1 in the body is complex and involves multiple transformation steps and hosts of Phase I (Cyp450) and Phase II (UDP-GT and GST) metabolic enzymes, proteins and nucleic acids in the liver (hepatocyte cells) before Aflatoxin B1 is biotransformed into its toxic metabolite Aflatoxin B1-exo-8,9-epoxide (AFBO). The AFBO interacts with DNA to form AFB-DNA adducts causing DNA breakages. The CYP1A2 is the principal metabolizer of Aflatoxin B1 at low concentrations while the reverse is true for CYP3A4. The accumulation of Aflatoxin B1 and AFBO also depletes the glutathione (GSH) due to the formation of high amounts of epoxides and other reactive oxygen species (ROS). These synergistic toxic events induces G:C to T:A transversions at certain sites in DNA and promotes tumorigenesis and ultimately hepatocellular carcinoma (HCC).

Currently, there are no known countermeasures that can selectively block or reduce Aflatoxin B1 toxicity after exposure, and the available options are only limited to relieve the resulting symptoms for individuals exposed to Aflatoxin B1. For example, atropine is used to treat Aflatoxin B1 poisoning that accompanies with emesis or abdominal pain. Among potential prophylactic agents, Oltripraz, an antischistosomal agent, has attracted most interest in recent years, but due to undesirable side effects and therapeutic costs it has limited long-term daily use.

This lack of effective countermeasures against Aflatoxin B1 toxicity is also of significant relevance to military. There is considerable evidence that Iraq weaponized Aflatoxin B1 in the 1980s. Though the resulting effects of using Aflatoxin B1 would be too slow to have a tactical advantage on the battlefield, it could still be used as a biological weapon to spread fear and panic in the general public and to contaminate food supplies to cause economic damage. Further the effects of inhaled Aflatoxin B1 from weapons and its co-exposure with other bioweapon toxins such as ricin, botulinum and enterotoxins, are not known. Hence, the demand for effective Aflatoxin B1 countermeasures is unmet which limits both the military biodefense security and pose grave danger to public health. Examples of treatments of Aflatoxin B1 toxicity include U.S. No. 2009/0249551 and U.S. No. 2003/0191137, which are incorporated herein by specific reference.

Thus, there is a need for a compounds and composition that can be used for mitigating effects of an aflatoxin-induced liver toxicity or injury.

SUMMARY

In some embodiments, a method for providing a therapy to a subject that has been exposed to an aflatoxin (e.g., Aflatoxin B1) can include: administering a compound having a structure of Formula 1 to the subject after exposure to the aflatoxin:

Formula 1 wherein: $R^1$, $R^2$, $R^3$, $R^4$, $R^5$ and/or $R^6$ are each individually a chemical moiety and n is 1, 2, 3, 4, or 5. In some aspects, $R^1$ includes a $C_1$-$C_{12}$ alkyl, secondary $C_1$-$C_{12}$ alkylamine or tertiary $C_1$-$C_{12}$ alkylamine, any substituted or unsubstituted; $R^2$ includes a $C_1$-$C_{12}$ alkyl or cycloalkyl, any substituted or unsubstituted; $R^3$ includes a hydroxyl, halogen, cyano, or $C_1$-$C_{12}$ alkylhydroxyl, substituted or unsubstituted; $R^4$ includes a hydrogen, hydroxy, halogen, cyano, phosphate, sulfate, $C_1$-$C_{12}$ alkyl, substituted or unsubstituted; $R^5$ includes a $C_4$-$C_6$ cycloalkyl or $C_4$-$C_6$ heterocycloalkyl, any substituted or unsubstituted; and $R^6$ includes hydrogen or $C_1$-$C_{12}$ alkyl, substituted or unsubstituted. In some aspects, the compound has a structure of Amprenavir or a derivative thereof, prodrug thereof, salt thereof, or stereoisomer thereof, or having any chirality at any chiral center, or tautomer, polymorph, solvate, or combination thereof. In some embodiments, the compound is an Amprenavir prodrug that has a structure of Amprenavir Phosphate:

In some embodiments, the Amprenavir is provided in a therapeutically effective amount to mitigate liver injury in the subject. In some aspects, the Amprenavir is provided in a therapeutically effective amount to inhibit onset of liver injury in the subject prior to detecting liver injury. I In some embodiments, the subject is exposed to Aflatoxin B1. In some aspects, the Amprenavir is provided in a therapeutically effective amount to inhibit transformation of the Aflatoxin B1 to Aflatoxin B1-exo-8,9-epoxide (AFBO) in the subject. In some aspects, the Amprenavir is provided in a therapeutically effective amount to inhibit AFBO interacting with DNA in the subject. In some aspects, the Amprenavir is provided in a therapeutically effective amount to inhibit G:C to T:A transversions in DNA in the subject. In some aspects, the Amprenavir is provided in a therapeutically effective amount to inhibit tumorigenesis in the subject. In some aspects, the Amprenavir is provided in a therapeutically effective amount to inhibit formation of hepatocellular carcinoma in the subject.

In some embodiments, the Amprenavir is provided in a therapeutically effective amount as a prophylactic prior to detecting liver injury in the subject. In some aspects, the Amprenavir is provided in a therapeutically effective amount after detecting liver injury in the subject to inhibit development of liver injury symptoms. In some aspects, the Amprenavir is provided in a therapeutically effective amount to reduce symptoms of liver injury in the subject. In some aspects, the Amprenavir is provided in a therapeutically effective amount to inhibit Aflatoxin B1 and/or AFBO from depleting glutathione in the subject. In some aspects, the Amprenavir is provided in a therapeutically effective amount to improve liver function of the subject after a liver injury from exposure to Aflatoxin B1.

In some embodiments, the Amprenavir is provided in a therapeutically effective amount of 120 mg to 2,800 mg per day. In some aspects, the Amprenavir is provided in a therapeutically effective amount of 0.1 mg/kg to 100 mg/kg of the subject. In some aspects, the Amprenavir is provided in a therapeutically effective amount at least once daily.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1 includes graphs of data for 3 week versus 6 week exposure to 10 ppm dietary Aflatoxin B1 for weight gain and food intake.

FIGS. 2A-2D include graphs of data for 6 week exposure to 10 ppm dietary Aflatoxin B1±Amprenavir: Survival (FIG. 34A), Indexed Weight (FIG. 34B), Food Intake (FIG. 34C), and Drug Intake (FIG. 34D).

FIG. 3 includes a graph of data for 6 week exposure to 10 ppm dietary Aflatoxin B1±Amprenavir for liver hydroxyproline reduction.

FIG. 4 includes a graph of data for 6 week exposure to 10 ppm dietary Aflatoxin B1±Amprenavir for Serum ALT.

FIG. 5 includes images of histology samples for 6 week exposure to 10 ppm dietary Aflatoxin B1±Amprenavir to illustrate representative liver histology.

FIGS. 6A-6D include graphs of data for 6 week exposure to 10 ppm dietary Aflatoxin B1±High dose Amprenavir: Weight (FIG. 38A), Indexed Weight (FIG. 38B), Food Intake (FIG. 38C), and Drug Intake (FIG. 38D).

FIG. 7 includes graphs of data for 6 week exposure to 10 ppm dietary Aflatoxin B1±High dose Amprenavir: Serum ALT, Liver hydroxyproline, and Sirius red.

FIG. 8 includes images of histology samples for 6 week exposure to 10 ppm dietary Aflatoxin B1±High dose Amprenavir: Liver Histology, All 6 Replicates (H&E, Picro Sirius Red).

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes compounds and/or materials (e.g., pharmaceutical compositions) for use to inhibit toxicity of an aflatoxin in a subject, such as a human or animal (e.g., domesticated farm animal). Inhibiting the toxicity of the aflatoxin can inhibit injury to an organ of the subject, such as the liver. The compounds can be included in materials for administration to a subject that has been exposed to an aflatoxin, or that is susceptible to aflatoxin toxicity or is experiencing aflatoxin toxicity. In some aspects, the compounds can be administered to a subject that has been exposed to an Aflatoxin B1, or that is susceptible to Aflatoxin B1 toxicity or is experiencing Aflatoxin B1 toxicity. The compounds can be administered to mitigate any adverse consequences that may arise from exposure to an aflatoxin, such as Aflatoxin B1.

Inhibiting liver injury or liver toxicity from the Aflatoxin B1, can also inhibit development or onset of cancer, such as liver cancer. The compounds can inhibit the liver injury from Aflatoxin B1 that occurs in the first few weeks, and also inhibit carcinogenesis of the liver that occurs or develops after the liver injury. As such, the compounds can be used for treating, inhibiting, or preventing hepatic fibrosis or cirrhosis or hepatocarcinoma.

In some embodiments, the compound can be administered to inhibit adverse physiological responses to mycotoxins, such as Aflatoxin B1, produced by *Aspergillus* species. In particular, the compound can be used to inhibit liver injury that is caused by Aflatoxin B1. In some aspects, the compound can be used to mitigate liver injury, so as to make the liver injury less severe, less serious, or less painful from a peak severity, peak seriousness, or peak painfulness. This allows the compounds to provide an improvement in physiological condition of a subject after exposure to Aflatoxin B1, such as improvement in liver function after having liver injury from the Aflatoxin B1. In some aspects, the compound can be used as a prophylactic to inhibit onset of liver toxicity or injury after or during exposure to Aflatoxin B1, which can mean that the compound is administered before onset of liver injury in an attempt to slow or stop the onset, development, or progression of liver injury. In some aspects, the compound can be used to treat a subject after onset of liver injury, such that the administration of the compound improves the liver function after a liver injury. That is, the liver can be identified as having an improved function by at least one measurable parameter after receiving treatment with the compound.

In some embodiments, the compound that can be used as a treatment for Aflatoxin B1 liver injury can be Amprenavir (also known as Agenerase), or a derivative thereof, prodrug thereof, salt thereof, or stereoisomer thereof, or having any chirality at any chiral center, or tautomer, polymorph, solvate, or combination thereof, as presented herein. Accordingly, the application of Amprenavir can be in the form of a medicine or other preparation (e.g., liver implant, liver depot, drug eluting tissue depot, etc.) that can be administered to a subject for prevention, inhibition, or slowing onset (e.g., as a prophylactic before symptoms after exposure to Aflatoxin B1) of Aflatoxin B1 liver injury or treatment of Aflatoxin B1 caused liver injury. The application of Amprenavir can be useful for modulating the action of one or multiple Cytochrome P450 enzymes, which can provide for the prophylactic action or treatment of Aflatoxin B1 caused liver injury. Accordingly, Amprenavir can be used in methods of treatment as a prophylactic for Aflatoxin B1 caused liver injury or treatment of Aflatoxin B1 caused liver injury.

In some embodiments, the use of Amprenavir in a therapy for Aflatoxin B1 induced liver injury can provide a new use of the U.S. Food and Drug Administration approved drug Amprenavir (also known as Agenerase and has IUPAC name: [(3S)-oxolan-3-yl] N-[(2S,3R)-4-[(4-aminophenyl)sulfonyl-(2-methylpropyl)amino]-3-hydroxy-1-phenylbutan-2-yl]carbamate). Now, Amprenavir can be used in mitigating the Aflatoxin B1 induced liver injury. Aflatoxin B1 is one of the most potent naturally occurring hepatotoxic and hepatocarcinogenic agents, and thereby a therapy for exposure can be beneficial. Accordingly, the compound can be used for a prophylactic or treatment of liver cancers, such as hepatocarcinoma.

In some embodiments, the compound can be used to inhibit Aflatoxin B1 transformation to its toxic metabolite Aflatoxin B1-exo-8,9-epoxide (AFBO). The AFBO interacts with DNA to form AFB-DNA adducts causing DNA breakages. The CYP1A2 is the principal metabolizer of Aflatoxin B1 at low concentrations while the reverse is true for CYP3A4. The accumulation of Aflatoxin B1 and AFBO also depletes the glutathione (GSH) due to the formation of high amounts of epoxides and other reactive oxygen species (ROS). These synergistic toxic events induces G:C to T:A transversions at certain sites in DNA and promotes tumorigenesis and ultimately hepatocellular carcinoma (HCC). Thus, the compound can inhibit any of these actions that are involved in liver toxicity or liver injury.

In some embodiments the therapy can include administering a medicament with a dosage of the amprenavir that ranges from 120 mg to 6000 mg per administration. In some aspects, the dosage can range from 10 mg/kg to 6000 mg/kg (e.g., mg amprenavir per kg of the subject). The dosage can be administered in one or more pharmaceutical dosage forms, known or developed in the art.

As a result of the dedicated investigations conducted by the present inventors to solve the above mentioned toxicity related issues of Aflatoxin B1, they have made the following findings. Specifically, as a result of search for substances that mitigate Aflatoxin B1 toxicity specifically hepatotoxicity, they have found that Amprenavir, which is a well-known FDA approved drug, reduces the Aflatoxin B1 hepatotoxicity. Amprenavir can also be provided as the phosphate prodrug thereof.

In some embodiments, the compound can be amprenavir as represented below, or a derivative thereof, prodrug thereof, salt thereof, or stereoisomer thereof, or having any chirality at any chiral center, or tautomer, polymorph, solvate, or combination thereof.

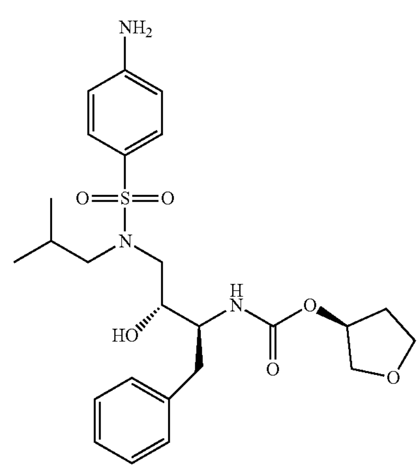

Amprenavir

In some embodiments, the compound can be the Amprenavir prodrug having a structure of Amprenavir Phosphate:

Amprenavir Phosphate

In some embodiments, the amprenavir or prodrug can be administered to solve or mitigate the toxic effects of Aflatoxin B1 by means of safe and effective therapeutic interventions.

Amprenavir was originally discovered by GlaxoSmithKline plc (GSK) as novel antiviral compound (WO 1998/056781A1, U.S. Pat. No. 6,730,679B1). Over the years, the polypharmacology (uses in other indications) effects of Amprenavir has been reported by others, in indications, such as (but not limited to), anti-inflammatory (CN 106139154A) and acute lung injury/acute respiratory distress syndrome and pulmonary fibrosis (CN 104083386A). However, it has not been known prior to the inventor's present invention that Amprenavir is capable of reducing the Aflatoxin B1 related toxicity or injury and may be used as a prophylactic after exposure to Aflatoxin B1 in an attempt to inhibit or delay onset of liver toxicity or injury.

EXAMPLES

Amprenavir was tested and showed excellent mitigation activity for liver histopathology (e.g., hepatocellular BrdU staining, serum transaminases, hydroxyproline levels) and hence was retested again in larger cohorts of the animals (6 rats per group). The results of these extended experiments were consistent with the results of an initial Amprenavir study (with 3 rats per group), showing significant or trends towards significant beneficial effects of Amprenavir on Aflatoxin B1-induced liver injury in rat models. The further analysis of transcriptomics data suggested that the effect of Amprenavir is meditated through Cyp enzymes, especially, Cyp2b2, Cyp1a1, Cyp3a18, Cyp3a9, Cyp2d2, Cyp2c7, Cyp2a3, Cyp2d1, Cyp2c24, Cyp4a2, all of which were greatly upregulated as a result of drug administration in rat livers. Hence, it is possible that that Amprenavir mechanism of action in reducing Aflatoxin B1 toxicity is through binding with Cyp enzymes, which in turn, reduce the biotransformation of Aflatoxin B1 to its toxic form AFBO.

Rat Model for Aflatoxin B1 Liver Injury

A study was performed with 12 rats to determine whether 3 weeks of dietary 10 ppm Aflatoxin B1 exposure is sufficient to detect liver injury. Accordingly, 3 rats were studied in each of the following 4 groups: no toxin, 3 week harvest; no toxin, 6 week harvest; 10 ppm dietary Aflatoxin B1, 3 week harvest; and 10 ppm dietary Aflatoxin B1, 6 week harvest. We harvested 1 set of animals (Aflatoxin B1 vs. control) at 3 weeks and harvested the 2nd set at 6 weeks. We then compared these groups for measures of liver injury to determine whether such injury is detectable after just 3 weeks of exposure. The collected biosamples were processed for H&E, Sirius Red, and BrdU tissue staining analyses and serum transaminase and albumin determinations. We selected time to test interventions over that shorter time frame. We reexamined samples harvested during the experiments described in our published study for liver hydroxyproline content. [Knipstein, B., et al., Dietary aflatoxin-induced stunting in a novel rat model: evidence for toxin-induced liver injury and hepatic growth hormone resistance. Pediatr Res, 2015. 78(2): p. 120-7] The analysis showed we can detect a significant increase in liver hydroxyproline after 6 weeks of exposure to 10 ppm Aflatoxin B1.

Aflatoxin B1 (Sigma-Aldrich, St. Louis, Mo.) was suspended in glycerol trioctanoate (Sigma-Aldrich) to create a stock solution (0.5 mg/mL), which was added to standard rodent chow (PicoLab Rodent Diet 20; LabDiet, St. Louis, Mo.) to create diets containing 10 ppm of Aflatoxin B1. Food, with and without Aflatoxin B1, was stored at 4° C. until placed in animal cages.

Three-week old (newly weaned) male inbred F344 Fischer or outbred Sprague-Dawley rats (Charles River Laboratory, Portage, Mich.) were housed in groups of three animals per cage for each level of toxin exposure under controlled light/dark cycles, and allowed ad libitum access to water and toxin-supplemented or vehicle-treated (i.e. control) chow throughout the experiment. Dietary consumption (per cage) was quantified daily and rats were weighed once or twice weekly. At 8-9 am on the day of the experimental endpoint, rats were injected with 100 mg/kg BrdU (Sigma-Aldrich) 1 hour prior to bleeding and sacrifice (from 9-10 am) for collection of sera and tissues. Liver tissue was immediately frozen in liquid nitrogen and stored at −80° C. or fixed in formalin for histological and immune-histochemical analyses (described in detailed in results Section).

Small bowel longitudinal length was measured and the proximal 25% isolated and processed for histological analysis of villous height. Briefly, the intestinal lumen was flushed with phosphate-buffered saline followed by 10% neutral-buffered-formalin, with the mucosal surface subsequently exposed by longitudinally incising the bowel; the proximal jejunum was pinned mucosal surface up on a wax tray and fixed in 10% formalin at 4° C. overnight; the tissue was subsequently covered with 2% agar, then cut into uniform sections, layered, and placed into a tissue cassette and in formalin for subsequent processing. Tibias were recovered and cleaned in 1 M NaOH prior to determination of tibial length, performed using a stadiometer.

The standardized animal models were used for efficacy testing of 5 selected repurposed drug candidates (e.g., Entospletinib, Quinapril, Tadalafil, Amprenavir, and Cyp3Cide) as identified by in vitro studies vs. no drug and no toxin controls on n=3 animals per toxin/drug/dose group. Subsequent drug-specific extended analyses (6 animals per group) were also performed on the top identified (most efficacious) hit based on pilot study results.

We completed an Aflatoxin B1 treatment study of 12 rats, along with tissue collection and some analyses. The comparison of 3 vs. 6 weeks of dietary 10 ppm Aflatoxin B1 exposure, begun at the time of weaning (i.e. age 3 weeks), to rats treated with control diets for effects on growth and liver injury. Analyses of those data showed the following.

FIG. 1 shows data for 3 vs. 6 week exposure to 10 ppm dietary Aflatoxin B1: Weight Gain and Food Intake. It was found that there was a decreased weight gain despite comparable food intake in Aflatoxin B1 toxin-exposed animals (FIG. 1B).

It was found that there was abnormal liver histopathology, consistent with our published study, in livers from animals exposed to dietary toxin for 6 weeks, but not 3 weeks. There is variable hepatocellular BrdU staining. Also, data showed that a 6 week exposure to 10 ppm dietary Aflatoxin B1 reduced Serum ALT compared to only 3 weeks. The data shows a trend towards increased serum transaminases in Aflatoxin B1- vs. control diet exposed animals at 3 and 6 weeks. The data also shows mild elevation of tissue hydroxyproline in animals exposed to 3 weeks of toxin- vs. control diet. Based on these results, we used the 6 week Aflatoxin B1 exposure regimen for the drug-treatment experiments described below in next section.

Aflatoxin B1 Toxicity Mitigation in Rats

Based on the in vitro analysis, we selected 4 FDA approved drugs and 1 chemical (Cyp3cide) to be tested in rats for Aflatoxin B1 mitigation. The tested compounds were: amprenavir; tadalafil; quinapril; cyp3cide; and entospletinib. Even though some of these drugs have been used/tested in humans and or animals, no literature evidence exists of their use in Aflatoxin B1 mitigation. Hence, we use the published literature that showed the oral doses used in rats for other indications. Based on that, for each drug we used approximated low, medium and high doses of to be tested for efficacy as shown in the following table.

| 1 | Amprenavir (Agenerase) | Oral: 20, 100, 400 mg/kg |
|---|---|---|
| 2 | Tadalafil (IC 351) | Oral: 2, 20, 200 mg/kg |
| 3 | Quinapril HCl | Oral: 2, 20, 200 mg/kg |
| 4 | Cyp3cide | Oral: 50 mg/kg |
| 5 | GS-9973 (Entospletinib) | Oral: 1 and 5 mg/kg |

It was found that Entospletinib is only mildly efficacious in mitigating Aflatoxin B1 induced toxicity or injury, and hence not further pursued with other doses. Overall our results did not show beneficial effects of Quinapril on Aflatoxin B1-induced growth impairment or hepatotoxicity. The results also did not show the beneficial effects of Tadalafil on growth, but does show a trend of lower liver hydroxyproline levels (a measure of liver fibrosis) in drug treated animals. It was also found that Cyp3cide did not reduce Aflatoxin B1-induced liver injury.

Figure 2A:
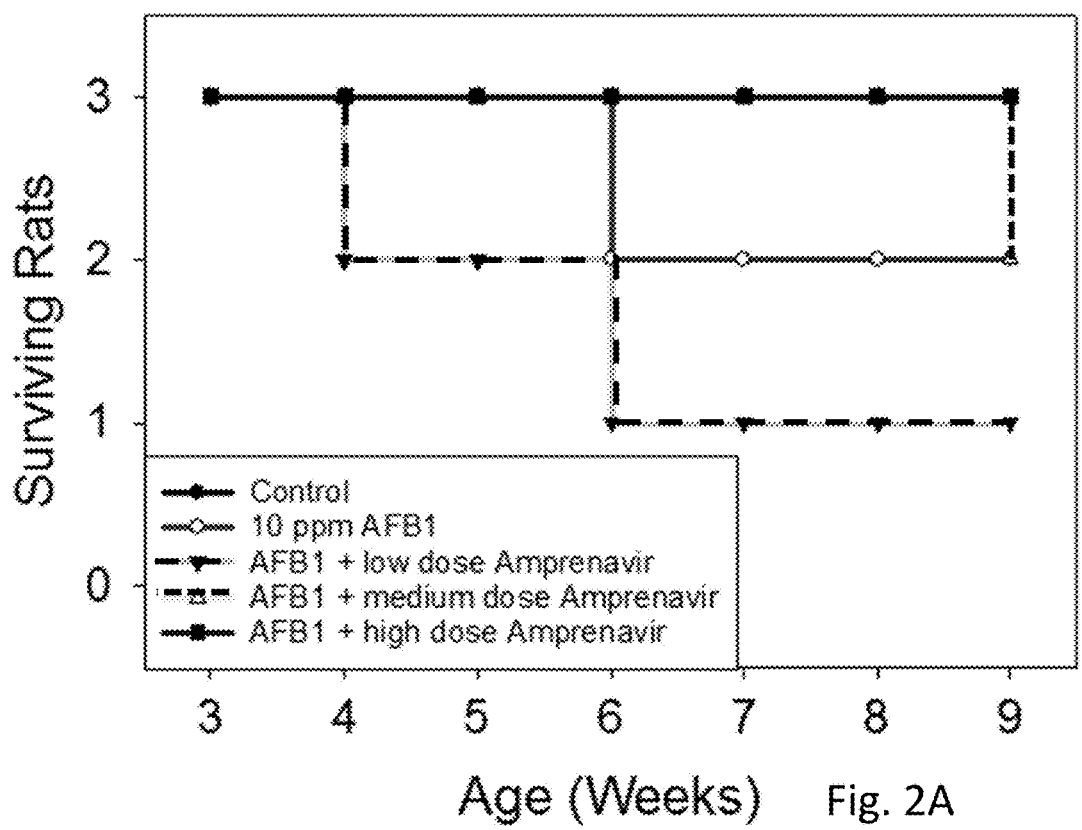
Figure 2B:
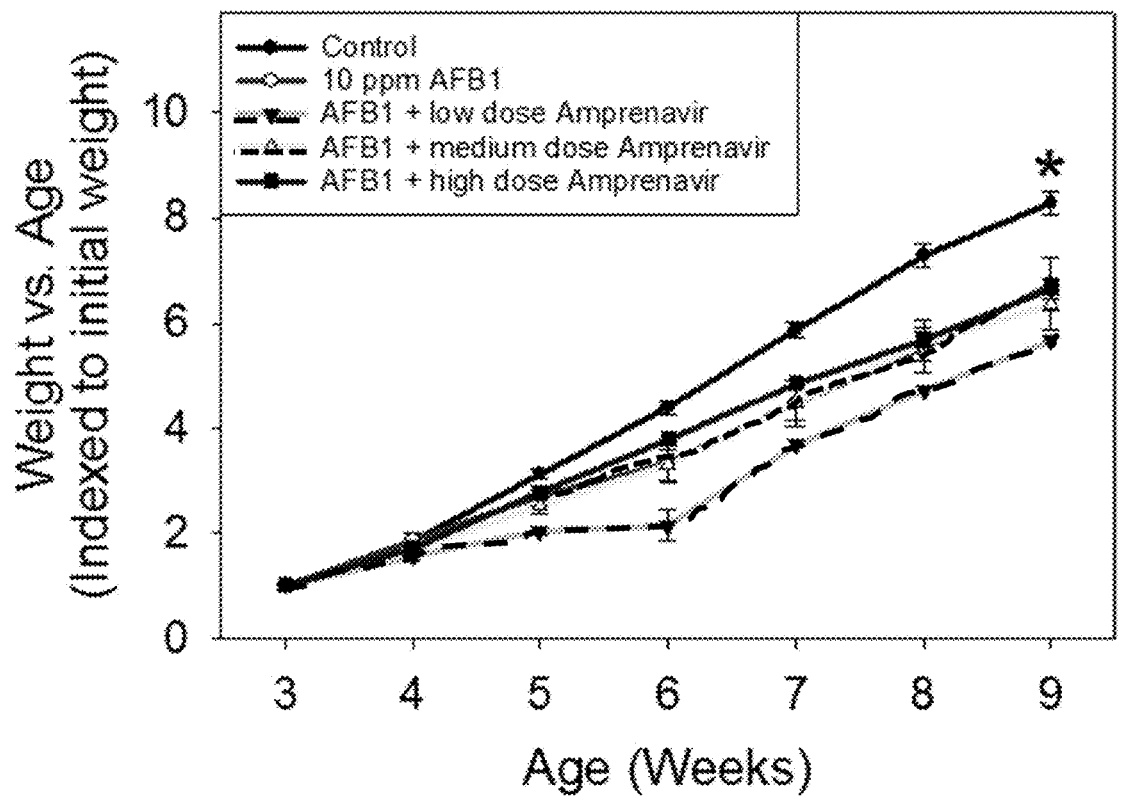
Figure 2C:
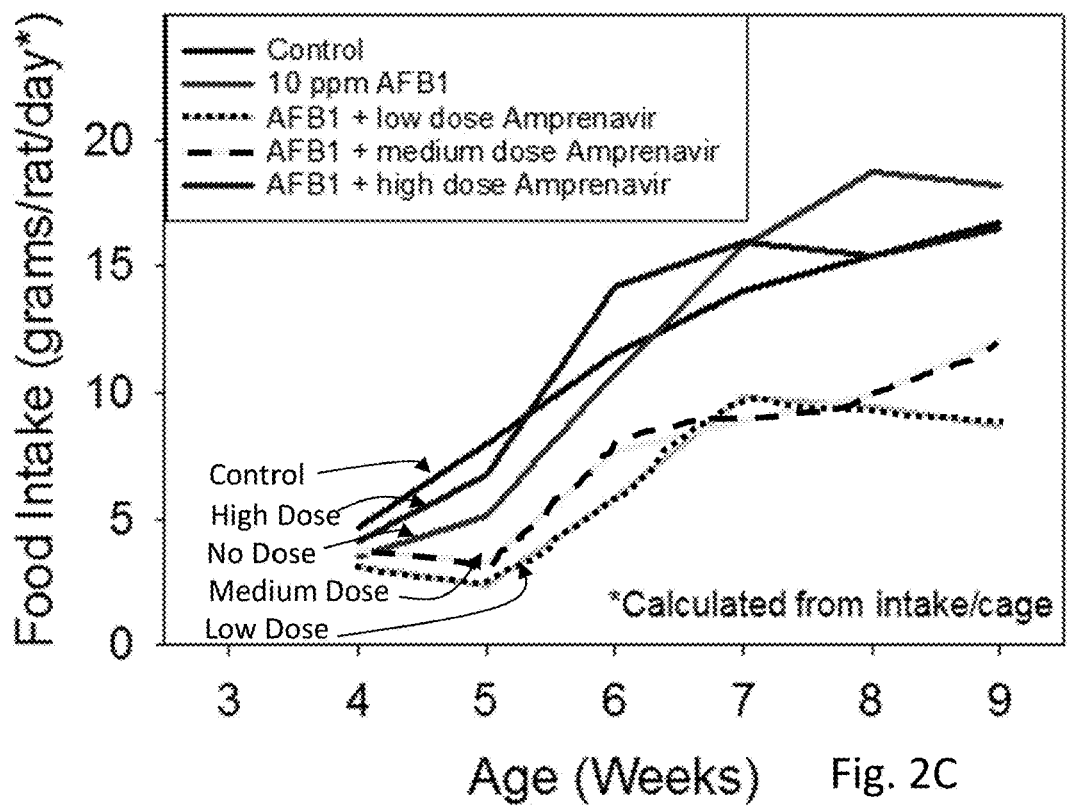
Figure 2D:
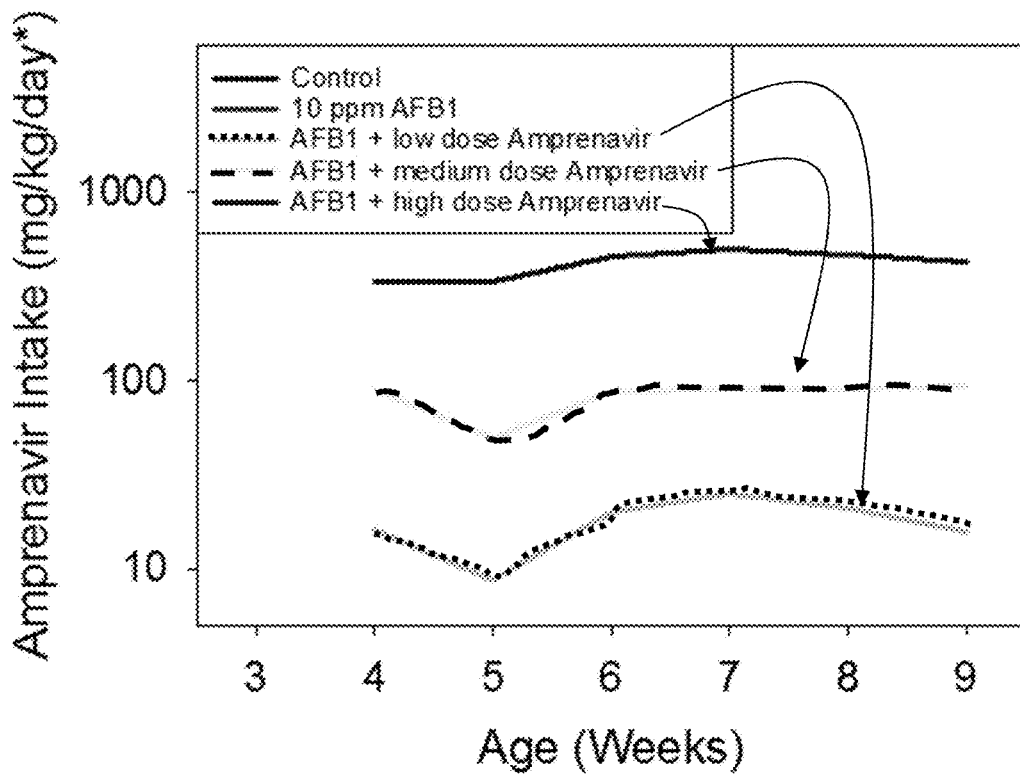

FIGS. 2A-2D provide results of analyses of Amprenavir in Aflatoxin B1-exposed rats. This study used rats that were euthanized for bio-sample harvest. In contrast to Entospletinib, Quinapril and Tadalafil, this experiment was notable for mortality during the course of the study (1 Aflatoxin B1-treated rat, 2 Aflatoxin B1-treated rats on low dose Amprenavir, and 1 Aflatoxin B1-treated rat on medium dose Amprenavir (FIG. 2A). Although final weights were different between groups by ANOVA, no pairwise comparisons showed significant differences (FIG. 2B). Food intake was lower in Aflatoxin B1-exposed rats on low and medium dose Amprenavir (FIG. 2C). Amprenavir exposures approximated target goals (FIG. 2D). FIGS. 2A-2D shows data for 6 week exposure to 10 ppm dietary Aflatoxin B1±Amprenavir: Survival, Indexed Weight, Food/Drug Intake.

Figure 3:
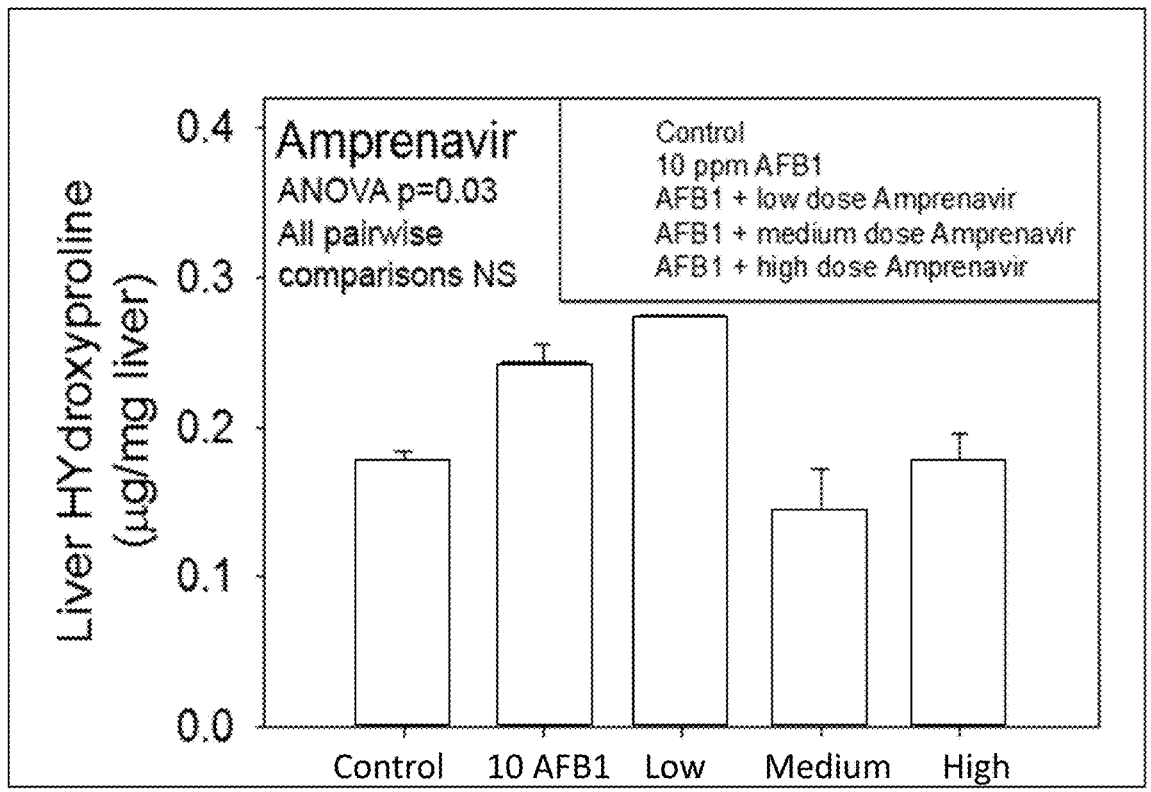

Liver hydroxyproline analysis showed significant differences between groups (ANOVA p=0.03) with trends towards decreased hydroxyproline in Amprenavir treated animals but no significant differences amongst pairwise comparisons (FIG. 3). FIG. 3 shows data for 6 week exposure to 10 ppm dietary Aflatoxin B1±Amprenavir: Liver hydroxyproline.

Figure 4:
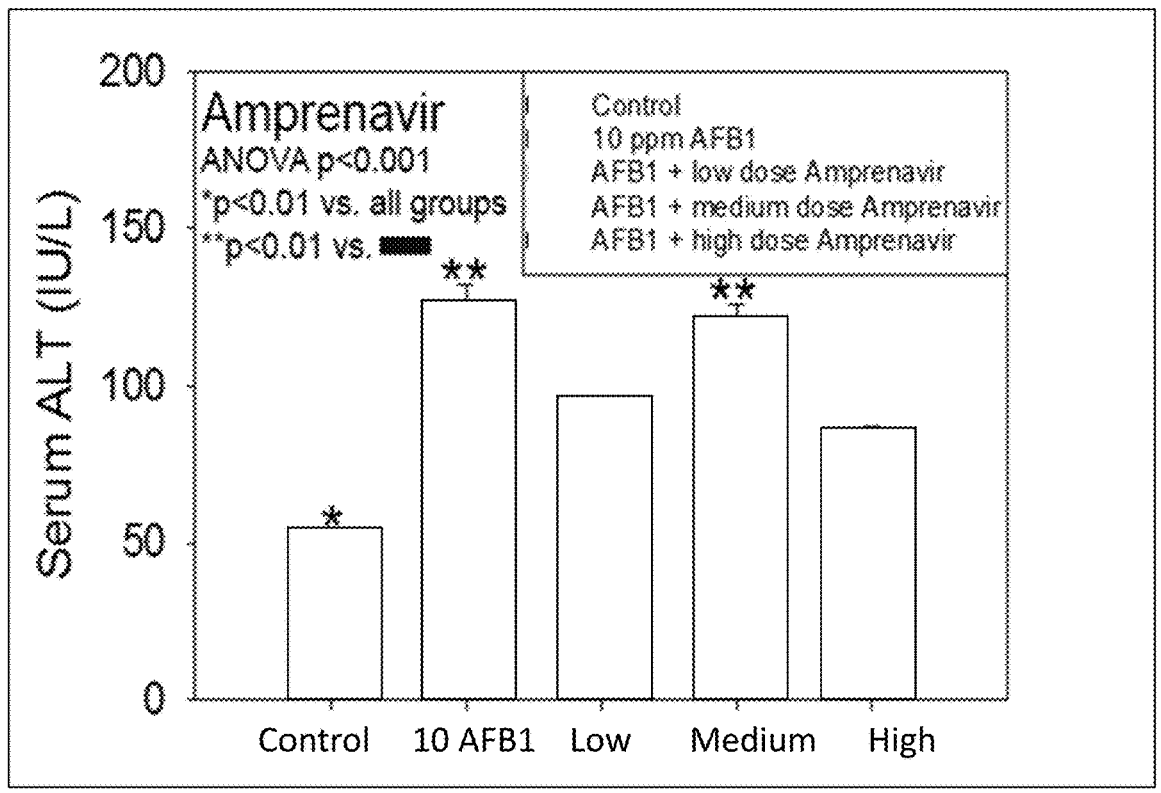
Figure 5:
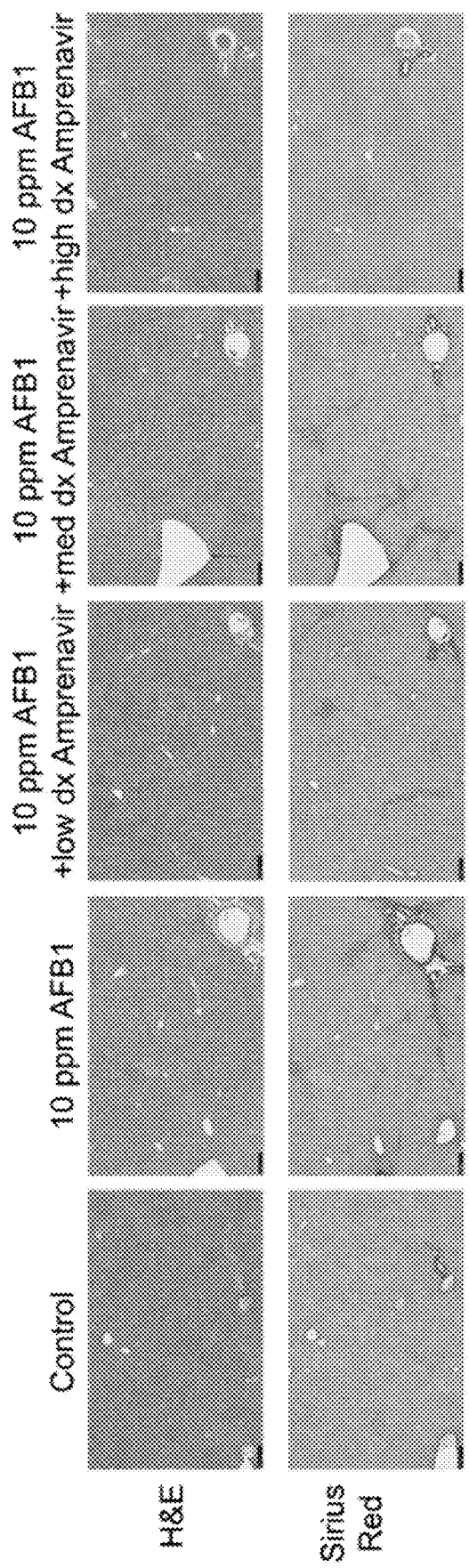
Figure 6A:
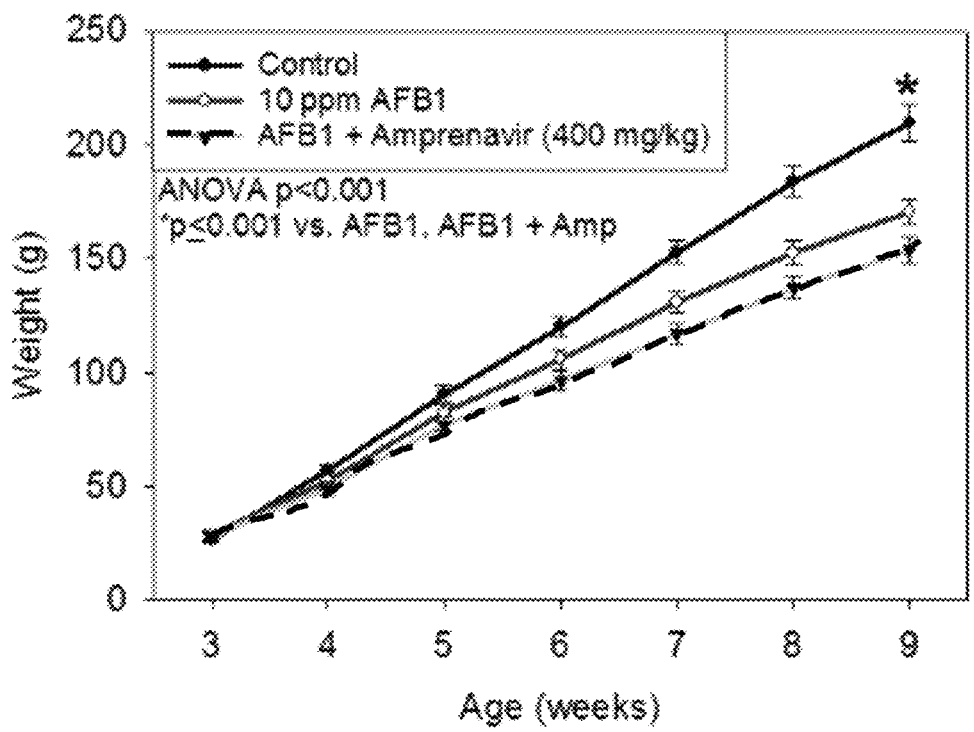
Figure 6B:
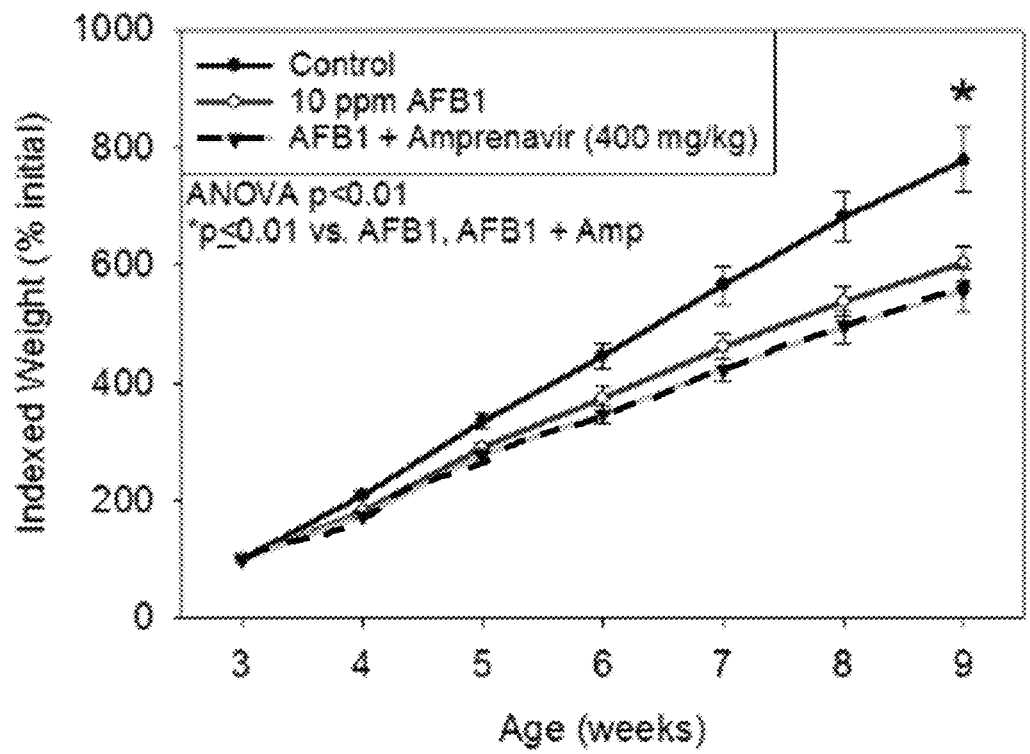
Figure 6C:
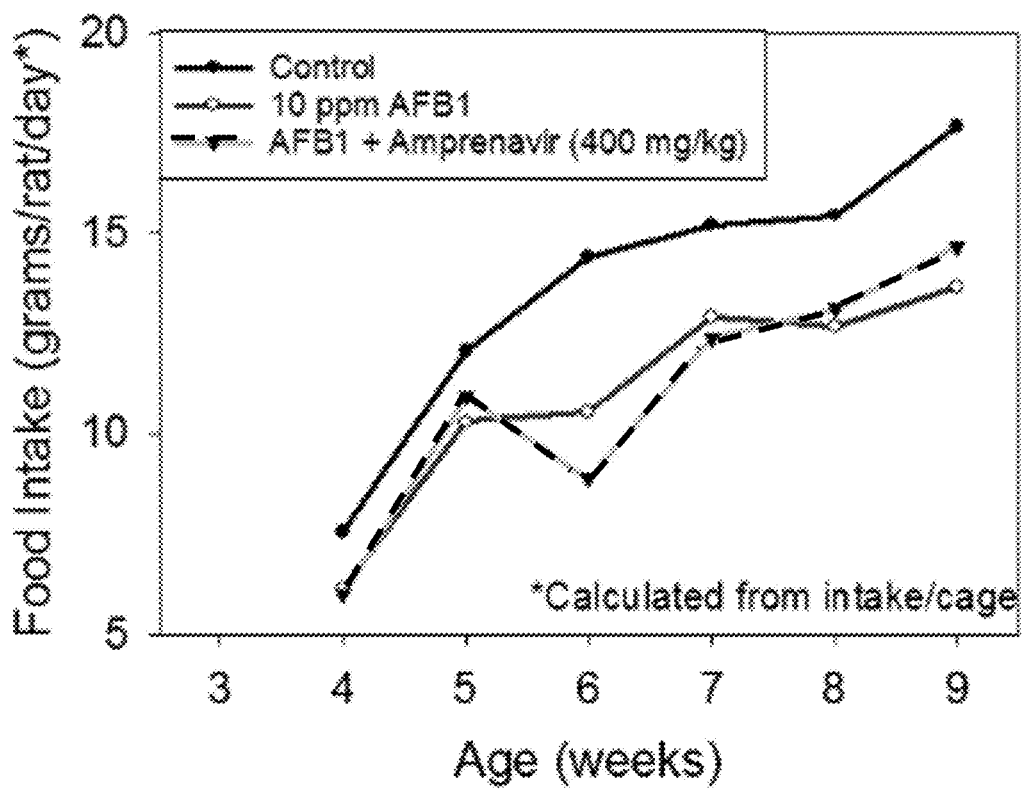
Figure 6D:
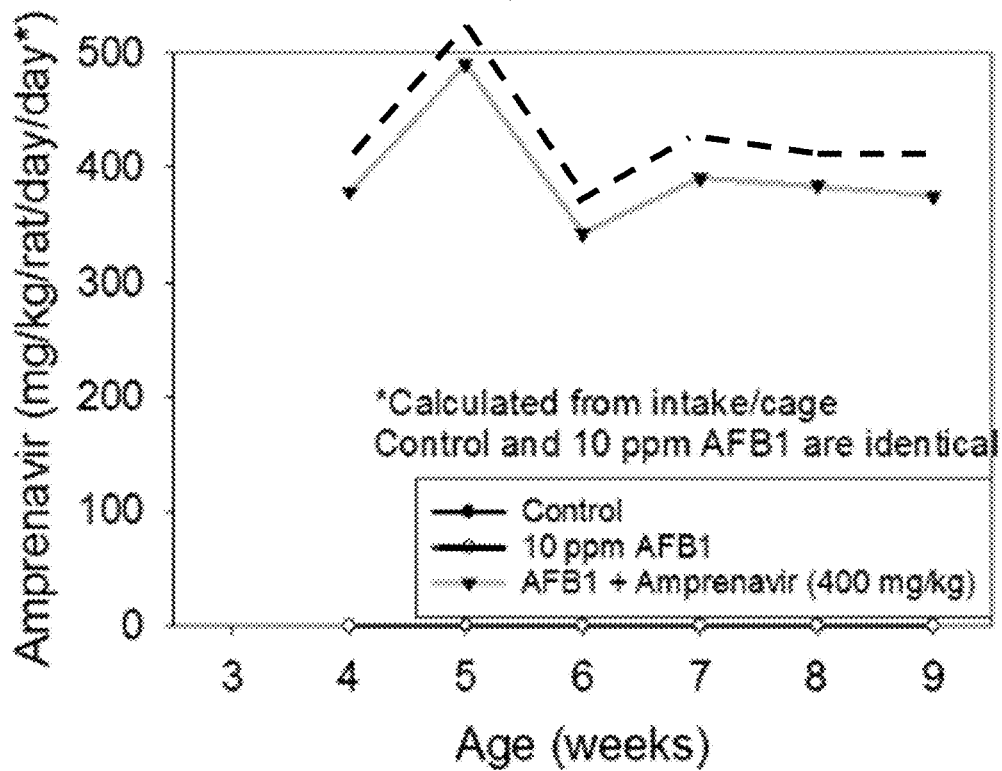
Figure 7:
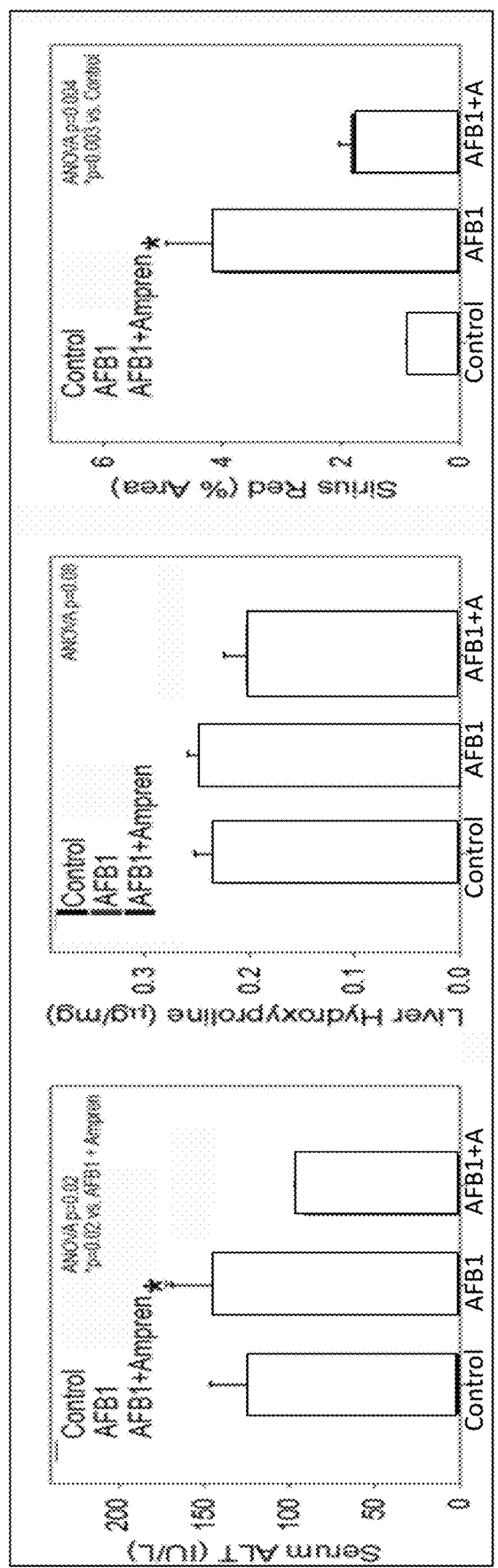
Figure 8:
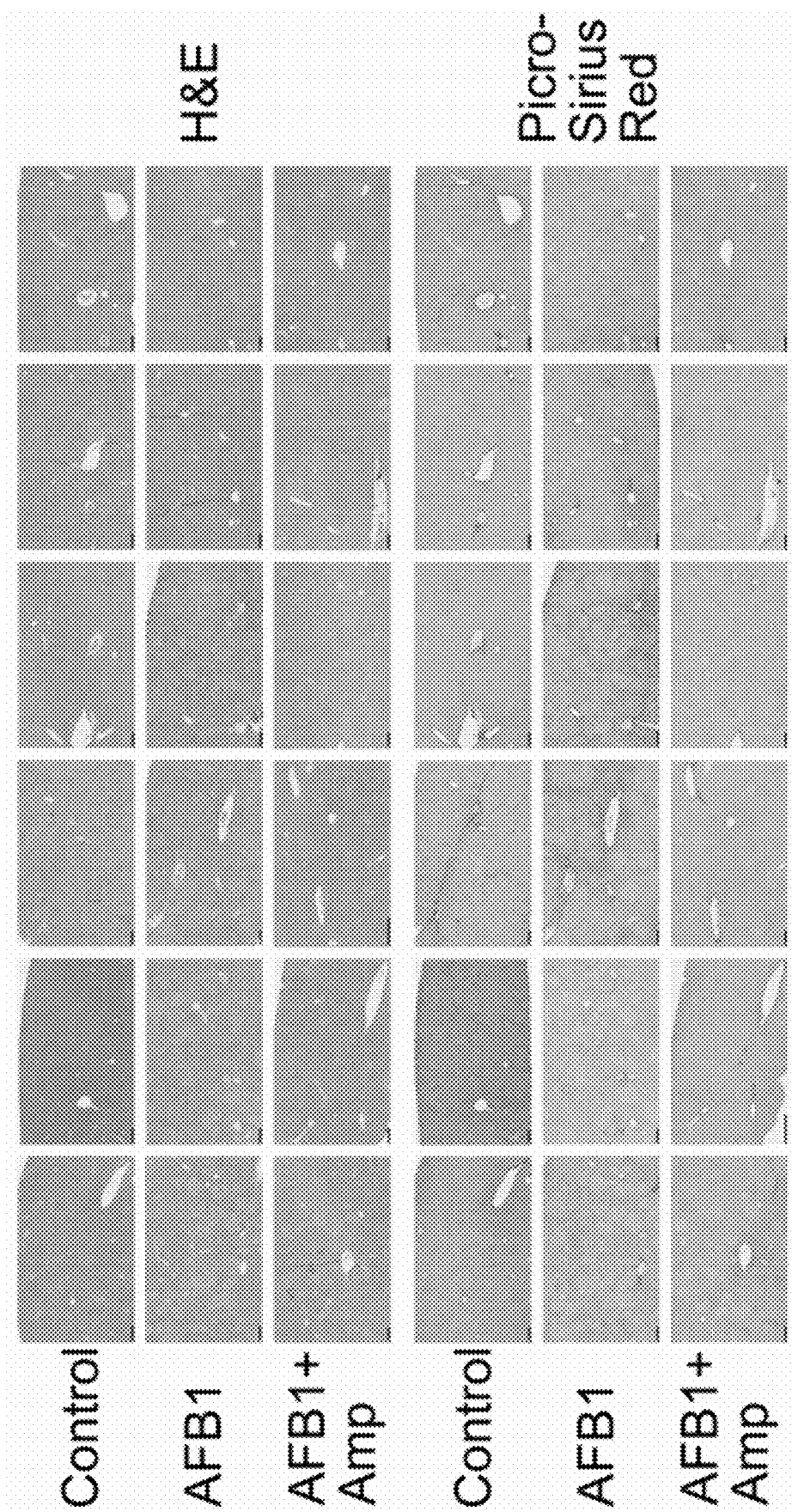

The results of Amprenavir showing reduced liver toxicity or injury after Aflatoxin B1 exposure is shown through the data of Liver histology (H&E, Sirius Red), immunohistochemistry (for BrdU), and serum ALT. Liver hydroxyproline analysis showed significant differences between groups (ANOVA p=0.03) with trends towards decreased hydroxyproline in Amprenavir treated animals, but no significant differences amongst pairwise comparisons (FIG. 3). Serum ALT levels were significantly lower in Aflatoxin B1-exposed rats given no Amprenavir or medium dose Amprenavir compared to Aflatoxin B1-exposed rats given high dose Amprenavir (FIG. 4). Similarly, inspection of liver histology shows decreased liver fibrosis, as assessed by Sirius Red staining, in Aflatoxin B1-exposed rats given high dose Amprenavir compared to those given no or medium dose Amprenavir (FIG. 5).

Overall the results of Amprenavir treatment show evidence of beneficial effects of high dose for mitigating Aflatoxin B1-induced liver injury, including improved survival (FIG. 2A-2S), lower serum transaminases (FIG. 3, FIG. 4), decreased liver fibrosis (FIG. 5) and a trend towards decreased liver hydroxyproline content (FIG. 3).

Amprenavir extended studies were performed. Our subsequent review of the collected in vivo data showed that Amprenavir is the most efficacious drug that should be retested again for an extended analysis and validation on larger cohorts of animals for Aflatoxin B1 mitigation effects. Hence, based on the promising effects of high dose Amprenavir on treating liver fibrosis in Aflatoxin B1-exposed rats, we further initiated extended studies to re-examine high dose Amprenavir (400 mg/kg) in more animals (n=6 Aflatoxin B1-treated and 6 Aflatoxin B1/Amprenavir-treated rats) after which we will have 8-9 animals in each of these groups: Aflatoxin B1+Vehicle, Aflatoxin B1+400 mg/kg Amprenavir, Vehicle only.

The gross appearance of the livers from the Aflatoxin B1/Amprenavir-treated vs. the Aflatoxin B1/Vehicle treated rats at the time of harvest were consistent with our impression when the rats were harvested in our earlier Amprenavir study (described above). As in that study, this experiment also showed that (i) there was no effect of Amprenavir on the Aflatoxin B1-induced reduction in weight gain, (ii) food intake was comparable in toxin compared to toxin+drug treated animals, (iii) Amprenavir treatment reduced serum ALT, and (iv) showed trends towards reducing liver hydroxyproline and morphometric measurement of liver fibrosis in Aflatoxin B1 treated rats (FIG. 2A-2D, FIG. 3, FIG. 4, and FIG. 5 versus FIG. 6A-6D, FIG. 7, and FIG. 8). In conclusion, this experiment is consistent with the results of the previous low dose Amprenavir study, showing significant or trends towards significant beneficial effects of Amprenavir on Aflatoxin B1-induced liver injury in rat models.

Compounds

In some embodiments, the amprenavir derivative can include a structure of Formula 1:

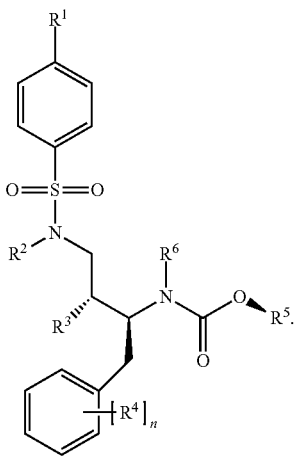

Formula 1

The structure of Formula 1 can include any substituent R group for $R^1$, $R^2$, $R^3$, $R^4$, $R^5$ and/or $R^6$, such as those described herein or otherwise known. The substituent can be a known chemical moiety as defined herein or known. The "n" is an integer, such as 1, 2, 3, 4, or 5. The structure of Formula 1 can include Amprenavir or Amprenavir Phosphate, and have the appropriate R groups.

In some embodiments, $R^1$ includes a $C_1$-$C_{12}$ alkyl, secondary $C_1$-$C_{12}$ alkylamine or tertiary $C_1$-$C_{12}$ alkylamine, any substituted or unsubstituted; $R^2$ includes a $C_1$-$C_{12}$ alkyl or cycloalkyl, any substituted or unsubstituted; $R^3$ includes a hydroxyl, halogen, cyano, or $C_1$-$C_{12}$ alkylhydroxyl, substituted or unsubstituted; $R^4$ includes a hydrogen, hydroxy, halogen, cyano, phosphate, sulfate, $C_1$-$C_{12}$ alkyl, substituted or unsubstituted; $R^5$ includes a $C_4$-$C_6$ cycloalkyl or $C_4$-$C_6$ heterocycloalkyl, any substituted or unsubstituted; and $R^6$ includes hydrogen or $C_1$-$C_{12}$ alkyl, substituted or unsubstituted.

In some embodiments of Formula 1, the R groups can be defined as follows: $R^1$ an amine; $R^2$ can be an alky; $R^3$ can be a hydroxyl or phosphate; $R^4$ can be a hydrogen, or other substituent; $R^5$ can be a $C_5$ heterocycloalkyl; and $R^6$ can be hydrogen or other substituent.

In some embodiments of Formula 1, the R groups can be defined as follows: $R^1$ can be a $C_1$-$C_{12}$ alkyl or a substituted secondary or tertiary $C_1$-$C_{12}$ alkylamine, or nitrogen bonded to one or more chemical moieties, such as $R^2$, substituted or unsubstituted; $R^2$ can be a $C_1$-$C_{12}$ alkyl or cycloalkyl, substituted or unsubstituted; $R^3$ can be a hydroxyl, halogen, cyano, $C_1$-$C_{12}$ alkylhydroxyl, substituted or unsubstituted; $R^4$ can be a hydrogen, hydroxy, halogen, cyano, $C_1$-$C_{12}$ alkyl, substituted or unsubstituted; $R^5$ can be a $C_4$-$C_6$ cycloalkyl, with or without a hetero atom, substituted or unsubstituted; and $R^6$ can be hydrogen or $C_1$-$C_{12}$ alkyl, substituted or unsubstituted.

In some embodiments, the R groups of Formula 1 including $R^1$, $R^2$, $R^3$, $R^4$, $R^5$ and/or $R^6$ are independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, and combinations thereof, and n is 1-5.

In some embodiments, the R groups of Formula 1 including $R^1$, $R^2$, $R^3$, $R^4$, $R^5$ and/or $R^6$ are independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, derivatives thereof, substituted or unsubstituted, any with or without hetero atoms, or combinations thereof as well as other well-known chemical substituents.

In some embodiments of Formula 1, each $R^1$, $R^2$, $R^3$, $R^5$, and $R^6$ are independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—NH$_2$), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—N⁺≡C⁻), cyanato (—O—C≡N), isocyanato (—O—N⁺≡C⁻), thiocyanato (—S—C≡N), isothiocyanato (—S—N⁺≡C⁻), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfonic acid (—SO$_2$—OH), sulfonato (—SO$_2$—O⁻)—$C_1$-$C_{24}$ alkylsulfanyl (—S-alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O—)), phospho (—PO$_2$), phosphino (—$PH_2$), any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any inducing rings, derivatives thereof, and combinations thereof.

Compositions

In some embodiments, a related aspect of the use of the compound is a pharmaceutical composition, the pharmaceutical composition including an effective amount of the compound of any embodiments of compounds of amprenavir, amprenavir derivative, amprenavir prodrug or Formula I (or pharmaceutically acceptable salt thereof) for treating a condition or as a prophylactic in an attempt to inhibit or delay onset of a condition; and where the condition is liver toxicity or injury from Aflatoxin B1 exposure.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of liver toxicity or injury from Aflatoxin B1 exposure.

As used herein, a "subject" or "patient" is a mammal, such as a cat, dog, rodent or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising any of the compounds of amprenavir, amprenavir derivative, amprenavir prodrug or Formula I disclosed herein and optionally a pharmaceutically acceptable carrier or one or more excipients or fillers. The compositions may be used in the methods and treatments described herein. Such compositions and medicaments include a therapeutically effective amount of any compound as described herein. The pharmaceutical composition may be packaged in unit dosage form. The unit dosage form is effective in treating a liver injury from Aflatoxin B1 exposure when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, or prodrug thereof with pharmaceutically acceptable carriers, excipients, binders, diluents or the like to prevent and treat a liver injury from Aflatoxin B1 exposure or provide prophylactic therefor. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir, such as a controlled delivery polymer depot. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts until the progression of the condition/disease state is decreased or stopped. The compounds of the present technology can be administered to a patient at dosage levels in the range of about 0.1 to about 18,000 mg per day, or up to about 5,000 mg per day, or up to about 3,000 mg per day, or up to about 2,800 mg per day, or up to 1,200 mg per day. An example includes a dosing of twenty-four 50 mg capsules, twice daily For a normal human adult having a body weight of about 70 kg, a dosage in the range of about 0.01 to about 1,000 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from 1×10-4 g/kg to 1 g/kg, preferably, 1×10-3 g/kg to 1.0 g/kg. Dosage of a compound of the present technology can also vary from 0.01 mg/kg to 100 mg/kg or, preferably, from 0.1 mg/kg to 10 mg/kg.

Definitions

By "substituted" as in "substituted alkyl," "substituted aryl," "substituted aromatic," and the like, as alluded to in some of the definitions provided herein, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

As used herein, "optionally substituted" indicates that a chemical structure may be optionally substituted with a substituent group, such as defined herein. That is, when a chemical structure includes an atom that is optionally substituted, the atom may or may not include the optional substituent group, and thereby the chemical structure may be considered to be substituted when having a substituent on the atom or unsubstituted when omitting a substituent from the atom. A substituted group, referred to as a "substituent" or "substituent group", can be coupled (e.g., covalently) to a previously unsubstituted parent structure, wherein one or more hydrogens atoms (or other substituent groups) on the parent structure have been independently replaced by one or more of the substituents. The substituent is a chemical moiety that is added to a base chemical structure, such as a chemical scaffold. As such, a substituted chemical structure may have one or more substituent groups on the parent structure, such as by each substituent group being coupled to an atom of the parent structure. The substituent groups that can be coupled to the parent structure can be any possible substituent group. In examples of the present technology, the substituent groups (e.g., R groups) can be independently selected from an alkyl, —O-alkyl (e.g. —$OCH_3$, —$OC_2H_5$, —$OC_3H_7$, —$OC_4H_9$, etc.), —S-alkyl (e.g., —$SCH_3$, —$SC_2H_5$, —$SC_3H_7$, —$SC_4H_9$, etc.), —NR'R", —OH, —SH, —CN, —$NO_2$, or a halogen, wherein R' and R" are independently H or an optionally substituted alkyl. Wherever a substituent is described as "optionally substituted," that substituent can also be optionally substituted with the above substituents.

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The term "boron compound" can include any compound having boron or radical thereof, or chemical having a boron substituent. Examples of boron compounds that can be included as the R groups defined herein are boron tri alkyl or radical thereof, boron di-alkyl radical, hydrogen boron di-alkyl, hydrogen boron alkyl radical, boric acid (e.g., H3BO3 or H2BO3 radical), borax (e.g., B4Na2O7.10H2O or radical thereof), boron sodium oxide (e.g., B4Na2O7 or radical thereof), boron oxide (e.g. B2O3 or radical thereof), boron acid zinc salt, cobalt borate neodecanoate complexes, boron zinc oxide (e.g., B6zn2O11 or radical thereof), boric acid sodium salt, perboric acid sodium salt, boron lithium oxide, ammonium boron oxide, boron silver oxide, boric acid lithium salt, boron trifluoride, boron difluoride radical, boron dihydroxy, potassium boron trifluoride, 4,4,5,5-tetramethyl-3,2-dioxaboralane, and radicals thereof. The radicals can be the R group and conjugated to the chemical scaffolds described herein.

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A method for providing a therapy to a subject that has been exposed to Aflatoxin B1, the method comprising:

administering a compound having a structure of Formula 1, salt thereof, or stereoisomer thereof, or having any chirality at any chiral center, or tautomer, polymorph, solvate, or combination thereof, to the subject after exposure to the Aflatoxin B1:

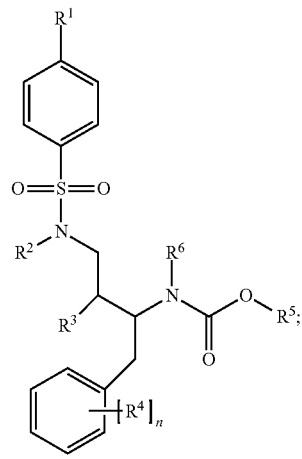

Formula 1 wherein:

$R^1$ is an amine, $R^2$ is an alkyl, $R^3$ is a hydroxyl or phosphate, $R^4$ is a hydrogen, hydroxy, halogen, cyano, phosphate, sulfate, $C_1$-$C_{12}$ alkyl, which is substituted or unsubstituted, $R^5$ is a $C_5$ heterocycloalkyl, $R^6$ is hydrogen, or $C_1$-$C_{12}$ alkyl, which is substituted or unsubstituted; and n is 1, 2, 3, 4, or 5.

2. The method of claim 1, wherein the compound has a structure of Amprenavir or a prodrug thereof, salt thereof, or stereoisomer thereof, or having any chirality at any chiral center, or tautomer, polymorph, solvate, or combination thereof:

Amprenavir

3. The method of claim 2, wherein the Amprenavir prodrug as a structure of Amprenavir Phosphate:

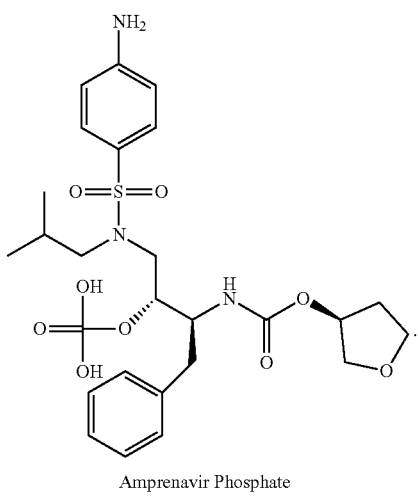

Amprenavir Phosphate

4. The method of claim 1, wherein the compound is provided in a therapeutically effective amount to mitigate liver injury in the subject.

5. The method of claim 1, wherein the compound is provided in a therapeutically effective amount to inhibit onset of liver injury in the subject prior to detecting liver injury.

6. The method of claim 1, wherein the subject is exposed to Aflatoxin B1.

7. The method of claim 6, wherein the compound is provided in a therapeutically effective amount to inhibit transformation of the Aflatoxin B1 to Aflatoxin B1-exo-8, 9-epoxide (AFBO) in the subject.

8. The method of claim 6, wherein the compound is provided in a therapeutically effective amount to inhibit AFBO interacting with DNA in the subject.

9. The method of claim 6, wherein the compound is provided in a therapeutically effective amount to inhibit G:C to T:A transversions in DNA in the subject.

10. The method of claim 1, wherein the compound is provided in a therapeutically effective amount to inhibit tumorigenesis in the subject.

11. The method of claim 1, wherein the compound is provided in a therapeutically effective amount to inhibit formation of hepatocellular carcinoma in the subject.

12. The method of claim 1, wherein the compound is provided in a therapeutically effective amount as a prophylactic prior to detecting liver injury in the subject.

13. The method of claim 1, wherein the compound is provided in a therapeutically effective amount after detecting liver injury in the subject to inhibit development of liver injury symptoms.

14. The method of claim 1, wherein the compound is provided in a therapeutically effective amount to reduce symptoms of liver injury in the subject.

15. The method of claim 6, wherein the compound is provided in a therapeutically effective amount to inhibit Aflatoxin B1 and/or AFBO from depleting glutathione in the subject.

16. The method of claim 6, wherein the compound is provided in a therapeutically effective amount to improve liver function of the subject after a liver injury from exposure to Aflatoxin B1.

17. The method of claim 1, wherein the compound is provided in a therapeutically effective amount of 120 mg to 2,800 mg per day.

18. The method of claim 1, wherein the compound is provided in a therapeutically effective amount of 0.1 mg/kg to 100 mg/kg of the subject.

19. The method of claim 1, wherein the compound is provided in a therapeutically effective amount at least once daily.

* * * * *